United States Patent [19]
Grabstein et al.

[11] Patent Number: 5,660,824
[45] Date of Patent: Aug. 26, 1997

[54] MUSCLE TROPHIC FACTOR

[76] Inventors: Kenneth H. Grabstein, 6121 86th Ave. SE., Mercer Island, Wash. 98040; LeBris S. Quinn, 6715 41st Ave. SW., Seattle, Wash. 98136; Anthony B. Troutt, 3412 238th St. SW., Brier, Wash. 98036

[21] Appl. No.: 535,733

[22] Filed: May 24, 1995

[51] Int. Cl.$^6$ .................................................. A61K 38/20
[52] U.S. Cl. ............................................ 424/85.2; 530/351
[58] Field of Search ............................. 424/85.2; 530/351

[56] References Cited

PUBLICATIONS

Science, vol. 264, 13 May 1994, pp. 965–968.

*Primary Examiner*—Howard E. Schain
*Attorney, Agent, or Firm*—Stephen L. Malaska

[57] ABSTRACT

Compositions and methods for stimulating muscle growth or differentiation in a vertebrate are disclosed. Such compositions include a muscle-trophic amount of interleukin-15 and can be used to treat a variety of conditions including disuse atrophy, wasting, various age-related disorders, secondary effects of diabetes, including glucose-intolerance, as well as muscular dystrophy, rhabdomyosarcoma and congestive heart failure. The compositions and methods of the invention find agricultural use in increasing the efficiency of meat and milk production of farm animals.

21 Claims, 4 Drawing Sheets

5,660,824

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 489 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..489

(xi) SEQUENCE DESCRIPTION: SEQ ID NO:1:

| ATG | AGA | ATT | TCG | AAA | CCA | CAT | TTG | AGA | AGT | ATT | TCC | ATC | CAG | TGC | TAC | 48 |
| Met | Arg | Ile | Ser | Lys | Pro | His | Leu | Arg | Ser | Ile | Ser | Ile | Gln | Cys | Tyr | |
| 1 | | | | 5 | | | | | 10 | | | | | 15 | | |

| TTG | TGT | TTA | CTT | CTA | AAC | AGT | CAT | TTT | CTA | ACT | GAA | GCT | GGC | ATT | CAT | 96 |
| Leu | Cys | Leu | Leu | Leu | Asn | Ser | His | Phe | Leu | Thr | Glu | Ala | Gly | Ile | His | |
| | | | 20 | | | | | 25 | | | | | 30 | | | |

| GTC | TTC | ATT | TTG | GGC | TGT | TTC | AGT | GCA | GGG | CTT | CCT | AAA | ACA | GAA | GCC | 144 |
| Val | Phe | Ile | Leu | Gly | Cys | Phe | Ser | Ala | Gly | Leu | Pro | Lys | Thr | Glu | Ala | |
| | | 35 | | | | | 40 | | | | | 45 | | | | |

| AAC | TGG | GTG | AAT | GTA | ATA | AGT | GAT | TTG | AAA | AAA | ATT | GAA | GAT | CTT | ATT | 192 |
| Asn | Trp | Val | Asn | Val | Ile | Ser | Asp | Leu | Lys | Lys | Ile | Glu | Asp | Leu | Ile | |
| | 50 | | | | | 55 | | | | | 60 | | | | | |

| CAA | TCT | ATG | CAT | ATT | GAT | GCT | ACT | TTA | TAT | ACG | GAA | AGT | GAT | GTT | CAC | 240 |
| Gln | Ser | Met | His | Ile | Asp | Ala | Thr | Leu | Tyr | Thr | Glu | Ser | Asp | Val | His | |
| 65 | | | | | 70 | | | | | 75 | | | | | 80 | |

| CCC | AGT | TGC | AAA | GTA | ACA | GCA | ATG | AAG | TGC | TTT | CTC | TTG | GAG | TTA | CAA | 288 |
| Pro | Ser | Cys | Lys | Val | Thr | Ala | Met | Lys | Cys | Phe | Leu | Leu | Glu | Leu | Gln | |
| | | | | 85 | | | | | 90 | | | | | 95 | | |

| GTT | ATT | TCA | CTT | GAG | TCC | GGA | GAT | GCA | AGT | ATT | CAT | GAT | ACA | GTA | GAA | 336 |
| Val | Ile | Ser | Leu | Glu | Ser | Gly | Asp | Ala | Ser | Ile | His | Asp | Thr | Val | Glu | |
| | | | 100 | | | | | 105 | | | | | 110 | | | |

| AAT | CTG | ATC | ATC | CTA | GCA | AAC | AAC | AGT | TTG | TCT | TCT | AAT | GGG | AAT | GTA | 384 |
| Asn | Leu | Ile | Ile | Leu | Ala | Asn | Asn | Ser | Leu | Ser | Ser | Asn | Gly | Asn | Val | |
| | | 115 | | | | | 120 | | | | | 125 | | | | |

| ACA | GAA | TCT | GGA | TGC | AAA | GAA | TGT | GAG | GAA | CTG | GAG | GAA | AAA | AAT | ATT | 432 |
| Thr | Glu | Ser | Gly | Cys | Lys | Glu | Cys | Glu | Glu | Leu | Glu | Glu | Lys | Asn | Ile | |
| | 130 | | | | | 135 | | | | | 140 | | | | | |

| AAA | GAA | TTT | TTG | CAG | AGT | TTT | GTA | CAT | ATT | GTC | CAA | ATG | TTC | ATC | AAC | 480 |
| Lys | Glu | Phe | Leu | Gln | Ser | Phe | Val | His | Ile | Val | Gln | Met | Phe | Ile | Asn | |
| 145 | | | | | 150 | | | | | 155 | | | | | 160 | |

| ACT | TCT | TGA | | | | | | | | | | | | | | 489 |
| Thr | Ser | | | | | | | | | | | | | | | |

(2) INFORMATION FOR SEQ ID NO:2:

(i) SEQUENCE CHARACTERISTICS:
(A) LENGTH: 162 amino acids
(B) TYPE: amino acid
(D) TOPOLOGY: linear (ii) MOLECULE TYPE: protein (xi) SEQUENCE DESCRIPTION: SEQ ID NO:2:

| Met | Arg | Ile | Ser | Lys | Pro | His | Leu | Arg | Ser | Ile | Ser | Ile | Gln | Cys | Tyr |
| 1 | | | | 5 | | | | | 10 | | | | | 15 | |

| Leu | Cys | Leu | Leu | Leu | Asn | Ser | His | Phe | Leu | Thr | Glu | Ala | Gly | Ile | His |
| | | | 20 | | | | | 25 | | | | | 30 | | |

| Val | Phe | Ile | Leu | Gly | Cys | Phe | Ser | Ala | Gly | Leu | Pro | Lys | Thr | Glu | Ala |
| | | 35 | | | | | 40 | | | | | 45 | | | |

| Asn | Trp | Val | Asn | Val | Ile | Ser | Asp | Leu | Lys | Lys | Ile | Glu | Asp | Leu | Ile |
| | 50 | | | | | 55 | | | | | 60 | | | | |

| Gln | Ser | Met | His | Ile | Asp | Ala | Thr | Leu | Tyr | Thr | Glu | Ser | Asp | Val | His |

| | 65 | | | | 70 | | | | 75 | | | | 80 | |
|---|---|---|---|---|---|---|---|---|---|---|---|---|---|---|
| Pro | Ser | Cys | Lys | Val 85 | Thr | Ala | Met | Lys | Cys 90 | Phe | Leu | Leu | Glu | Leu 95 | Gln |
| Val | Ile | Ser | Leu 100 | Glu | Ser | Gly | Asp | Ala 105 | Ser | Ile | His | Asp | Thr 110 | Val | Glu |
| Asn | Leu | Ile 115 | Ile | Leu | Ala | Asn | Asn 120 | Ser | Leu | Ser | Ser | Asn 125 | Gly | Asn | Val |
| Thr | Glu 130 | Ser | Gly | Cys | Lys | Glu 135 | Cys | Glu | Glu | Leu | Glu 140 | Glu | Lys | Asn | Ile |
| Lys 145 | Glu | Phe | Leu | Gln | Ser 150 | Phe | Val | His | Ile | Val 155 | Gln | Met | Phe | Ile | Asn 160 |
| Thr | Ser | | | | | | | | | | | | | | |

MUSCLE TROPHIC FACTOR

FIELD OF THE INVENTION

The invention is directed to muscle growth, and in particular, to methods of stimulating muscle growth or differentiation in mammals by administering an effective mount of interleukin-15.

BACKGROUND OF THE INVENTION

Since nuclei in muscle fibers of vertebrate animals are incapable of DNA synthesis or mitotic division, increases in muscle fiber numbers or in numbers of muscle fiber nuclei are due to proliferation and subsequent differentiation of skeletal muscle precursor cells known as "myoblasts." In adults, myoblasts remain as a mitotically quiescent reserve precursor population which can, upon muscle injury, re-enter the cell cycle, undergo several rounds of proliferation, and subsequently differentiate and permanently exit the from the cell cycle. Upon differentiation, differentiated myoblasts ("myocytes") acquire the ability to fuse with one another or with muscle fibers, and also commence coordinate expression of a large set of muscle-specific myofibrillar and contractile proteins (e.g., muscle myosins and actin, troponin, tropomyosin, etc.).

Muscle tissue can grow by several different mechanisms which are controlled by different trophic factors. Muscle tissue can grow by hypertrophy, an enlargement of or increase in mass or size of muscle fibers, or by hyperplasia, an increase in the numbers of fibers or in the numbers of muscle nuclei, or by a combination of these two processes. Growth factors that act on skeletal muscle tissue can be divided into two broad groups. The factors that stimulate proliferation of myoblasts usually inhibit differentiation of myoblasts and inhibit the expression and action of the muscle regulatory transcription factors (MRFs). Conversely, the factors that stimulate differentiation of myoblasts usually stimulate expression of the MRFs and can contribute to muscle hypertrophy. Most pharmacologic agents currently under consideration as muscle trophic factors act to stimulate muscle hypertrophy. Such hypertrophic factors include, for example, growth hormone (GH) or insulin-like growth factor-I (IGF-I). Muscle hypertrophy can be assessed by the measurement of muscle fiber diameter in vivo or in vitro, or by the measurement of the accretion of the muscle-specific myofibrillar and contractile proteins.

Clinically, a decline in such skeletal muscle tissue mass, or muscle atrophy, is an important contributor to frailty in older individuals. In human males, muscle mass declines by one-third between the ages of 50 and 80. In older adults, extended hospitalization can result in further disuse atrophy leading to a potential loss of the ability for independent living and to a cascade of physical decline. Moreover, the physical aging process profoundly affects body composition, including significant reductions in lean body mass and increases in central adiposity. The changes in overall adiposity and fat distribution appear to be important factors in many common "age-related" disorders such as hypertension, glucose intolerance and diabetes, dyslipidemia, and atherosclerotic cardiovascular disease. In addition, it is possible that the age-associated decrement in muscle mass, and subsequently in strength and endurance, may be a critical determinant for functional loss, dependence and disability. Muscle weakness is also a major factor predisposing the elderly to falls and the resulting morbidity and mortality. Complications from falls constitute the sixth leading cause of death among people over 65 years of age.

Treatment of musculoskeletal frailty with trophic factors such as growth hormone or IGF-I can be associated with significant deleterious side effects including salt retention, edema, elevations in blood pressure, insulin resistance, hyperglycemia, hypoglycemia, gynecomastia, carpal tunnel syndrome and disuse myalgias/arthralgias. Such side effects are likely due to the pleiotrophic effects of these factors on many tissues and metabolic processes. Similarly, treatment with estrogens or androgens, which in some studies have been shown to increase muscularity or bone density, may coincidentally increase the risk of neoplasms. Thus, there exists a need for a muscle-trophic factor that has more specific actions to stimulate muscle hypertrophy, and ultimately, muscle mass. Measures that reduce or reverse the loss of skeletal muscle mass will lead to increased capacity for independence for elderly individuals and thus increased quality of life, as well as a reduction in health care expenditures. A factor that does not stimulate myoblast proliferation would be of particular value.

SUMMARY OF THE INVENTION

The invention is directed to a muscle-trophic factor, and its use in stimulating muscle growth or differentiation in mammals. In particular, the invention is directed to a the use of interleukin-15 (IL-15) to stimulate muscle growth, differentiation or hypertrophy. Such stimulation of muscle growth is useful for treating atrophy, or wasting, in particular, skeletal muscle atrophy and cardiac muscle atrophy. In addition, certain diseases wherein the muscle tissue is damaged, is abnormal or has atrophied, are treatable using the invention, such as, for example, normal aging, disuse atrophy, wasting or cachexia, and various secondary disorders associated with age and the loss of muscle mass, such as hypertension, glucose intolerance and diabetes, dyslipidemia and atherosclerotic cardiovascular disease. In addition, IL-15 may be used to treat rhabdomyosarcomas since IL-15 may induce myoblast differentiation. The invention also is directed to the treatment of certain cardiac insufficiencies, such as congestive heart failure. The treatment of muscular myopathies such as muscular dystrophies is also embodied in the invention.

In general, the method of the invention comprises administering to a vertebrate an amount of IL-15 effective to stimulate the needed muscle growth or differentiation. Further included in the invention are compositions that comprise such a muscle-trophic amount of IL-15 alone or in combination with at least one other muscle-trophic factor, for example, steroids, growth hormone or IGF-I. Methods of treatment that provide for the administration of a muscle-trophic amount of IL-15 and a muscle-trophic amount of another factor, such as steroids, growth hormone or IGF-I are also provided by this invention. Relative to animal agriculture, the invention provides compositions and methods of inducing skeletal muscle growth in a vertebrate in order to increase the efficiency of meat production in animal agriculture.

DETAILED DESCRIPTION OF THE INVENTION

Figure 1A:
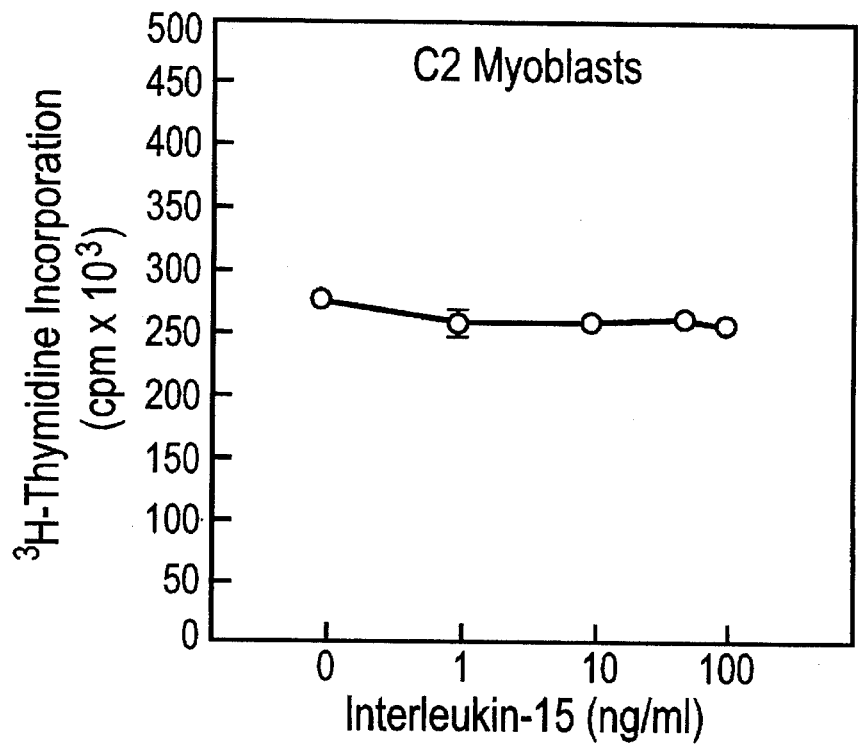
FIG. 1 shows the effects of IL-15 on myoblast proliferation. Proliferation was assayed by $^3$[H]-thymidine incorporation into DNA using mouse C2 myoblasts (FIG. 1A), or primary bovine myogenic cultures (FIG. 1B). Data points represent the means of two dishes ± SEM for each concentration of IL-15. In cases where no error bars are apparent, SEM is smaller than symbol size. Data shown are representative of experiments performed five times for C2 myoblasts and twice for bovine primary cultures.

Interleukin-15 ("IL-15") is a known T-cell growth factor that can support proliferation of an IL-2-dependent cell line, CTLL-2. IL-15 was first reported by Grabstein et al., in *Science*, 264:965 (1994), which is incorporated herein by reference, as a 114-amino acid mature protein. The cDNA of human IL-15 is shown in SEQ ID NO:1, whereas the amino acid sequence of human IL-15 is shown in SEQ ID NO:2. The term, "IL-15" as used herein, means a polypeptide having at least 90% homology to the native amino acid sequence of SEQ ID NO:2; and muteins, analogs or subunits of the native polypeptides that are encoded by nucleic acids that bind to the nucleic acid sequence of SEQ ID NO:1 under conditions of moderate or high stringency, and each of which will stimulate proliferation of CTLL-2 cells (Gillis and Smith, *Nature* 268:154 (1977); ATCC TIB 214). In the CTLL-2 proliferation assays, supernatants of cells transfected with recombinantly expressed precursor and inframe fusions of mature forms of IL-15 can induce CTLL-2 cell proliferation. The term, IL-15, as used herein, also means IL-15 as derived from a variety of mammalian species, including, for example, human, simian, bovine, porcine, equine and murine. An IL-15 "mutein" or "variant", as referred to herein, is a polypeptide substantially homologous to a sequence of a native mammalian IL-15 but that has an amino acid sequence different from a native mammalian IL-15 polypeptide because of an amino acid deletion, insertion or substitution. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-15 variants are also encompassed by the invention. Examples of such variants are proteins that result from alternate mRNA splicing events or from proteolytic cleavage of the IL-15 protein, wherein the IL-15 binding property is retained. Alternate splicing of mRNA may yield a truncated but biologically active IL-15 protein. Variations attributable to proteolysis include, for example, differences in the N- or C-termini upon expression in different types of host cells, due to proteolytic removal of one or more terminal amino acids from the IL-15 protein (generally from IL-5 terminal amino acids).

Human IL-15 can be obtained according to the procedures described by Grabstein et al., *Science*, 264:965 (1994), or by conventional procedures such as polymerase chain reaction (PCR) based on DNA sequence information provided in SEQ ID NO:1. A deposit of human IL-15 cDNA was made with the American Type Culture Collection, Rockville, Md., USA (ATCC) on Feb. 19, 1993 and assigned accession number 69245. The deposit was named "I41-hIL-15." The deposit was made according to the terms of the Budapest Treaty.

As used herein, "myoblast cultures" refers to cultures that contain cycling skeletal muscle precursors, and are considered distinct from "muscle fiber cultures" which are derived from myoblast cultures that are allowed to undergo differentiation and fusion to form multinucleated muscle fibers. The term "myogenic culture" is a generic term that refers to both kinds of cultures. The term "myocyte" refers to a differentiated, post-mitotic, muscle cell that has not yet undergone fusion, and thus represents, in general, a transient cell type under most conditions.

The term "muscle-trophic" means the accumulation by muscle of contractile protein, resulting in an increase in the mass or size of muscle fiber relative to the mass or size of such muscle fiber prior to the accumulation by muscle of contractile protein. The term "muscle-trophic amount" as used herein with respect to a trophic factor such as IL-15, a steroid, IGF-I or growth hormone, means that amount of IL-15, a steroid, IGF-I or growth hormone that is sufficient to cause a muscle fiber to increase in mass or size relative to the mass or size of such muscle fiber prior to administration of the trophic factor.

"Myosin heavy chain", or "MHC", is muscle-specific myosin heavy chain, a muscle-specific contractile protein expressed by muscle fibers. The MHC protein represents a major portion of the total myofibrillar protein produced by muscle fibers, and therefore is a good measure of myofibrillar protein accretion. Accumulation of the MHC protein by differentiated myocytes and muscle fibers is an indication of skeletal myogenic differentiation and muscle hypertrophy. See, for example, Bader et al., *J. Cell Biol.* 95:763–770 (1982) and Chi et al., *Proc. Natl. Acad. Sci. USA*, 72:4999–5003 (1975).

The term "steroid" refers to an anabolic steroid hormone such as an estrogen or an androgen, or a derivative thereof.

Because muscle-specific myosin heavy chain protein is a marker of terminal muscle differentiation, a quantitative method for detecting MHC synthesis is an important resource for identifying muscle hypertrophy. In order to detect MHC synthesis, conventional Western blot techniques can be used, such as those described in Quinn et al., *J. Cell Physiol.*, 159:387 (1994) using a monoclonal antibody, such as, MF-20 described by Bader et al., *J. Cell Biol.*, 95:763 (1982). Monoclonal antibody MF-20 has binding affinity for MHC and is publicly available from Developmental Studies Hybridoma Bank, Iowa City, Iowa. Alternatively, any monoclonal antibody that is specific for MHC would find use in a Western blot analysis for detecting MHC. Indeed, substantially purified MHC, or any of the other muscle-specific protein, e.g., actin or troponin, can be used to generate novel monoclonal antibodies against such muscle-specific protein that can be useful in such Western blot analyses. Such Western blots techniques and reagents are well known in the art.

Alternatively to using a Western blot analysis for detecting MHC synthesis, and thus muscle hypertrophy, differentiated myocytes and muscle fibers can be detected using immunofluorescent detection of muscle-specific MHC as described by Quinn et al., *J. Cell Physiol.*, 159:387 (1994). In general, cultures are rinsed with serum-free culture medium, fixed, rinsed again with culture medium, then blocked with a buffered saline solution containing a small percentage of serum. Cultures then can be incubated with a buffered saline solution containing a monoclonal antibody against MHC, for example, MF-20, rinsed and incubated with a labeled, e.g., fluorochrome, anti-mouse IgG. At the end of the incubation, a nuclear staining agent, such as ethidium bromide, can be added. Cultures are rinsed, mounted in glycerol, and viewed using epifluorescence optics. The number of myocyte nuclei (nuclei within MHC-positive cells) per microscopic field then can be determined.

In addition to the above, the invention also comprises the administration of a muscle-trophic amount of IL-15 protein to a vertebrate in need thereof. Administration of IL-15 can be performed alone or in concurrent or sequential combination with an effective The invention also provides methods of using compositions comprising a muscle-trophic mount of IL-15 in a suitable diluent or carrier. The IL-15 of the invention can be formulated according to known methods used to prepare pharmaceutical compositions. The IL-15 can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical *Sciences*, 16th ed. 1980, Mack Publishing Co. In addition, such compositions can contain IL-15 complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, alginate beads, erythrocyte ghosts or spheroblasts. Such compositions will influence the physical state, solubility, stability, rate of in vivo release, and rate of in vivo clearance of IL-15. The IL-15 molecule can also be conjugated to antibodies against tissue-specific receptors, ligands or antigens, or coupled to ligands of tissue-specific receptors.

In addition, IL-15 compositions can be administered topically, orally, parenterally, rectally, by inhalation or by direct gene transfer. The term "parenteral" includes subcutaneous injections, intravenous, intramuscular, intracisternal injection, or infusion techniques. The term "direct gene transfer" means the administration of an expression vector or plasmid containing the gene for IL-15 directly into the target tissue, see for example, Wolff et al., *Science*, 247:1465 (1990), incorporated herein by reference. Such compositions will typically contain an effective amount of IL-15, alone or in combination with an effective amount of any other active material. The dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices without undue experimentation.

By virtue of this inventive method, the treatment of certain conditions such as congestive heart failure, rhabdomyosarcoma, disuse atrophy, wasting or cachexia, diabetes, normal aging, and the treatment of certain conditions associated with reductions in muscle mass of older-aged animals, such as hypertension, diabetes, and artherosclerotic cardiovascular disease are possible. Further, such treatment may also alleviate secondary side effects associated with the above-listed conditions. In addition, the treatment of muscular myopathies, such as muscular dystrophies are encompassed by the invention. Muscular dystrophy can be characterized by progressive muscle weakness, destruction and regeneration of the muscle fibers, and eventual replacement of the muscle fibers by fibrous and fatty connective tissue. There is no accumulation of metabolic storage material in the muscle fibers of patients suffering from muscular dystrophy. Treatment according to the invention may alleviate some of the symptoms of the disease and provide improved quality of life for the patients.

Further, the invention may also find use for increasing the efficiency of animal meat production. Specifically, animals may be fed or injected with a muscle-trophic amount of IL-15 in order to increase overall skeletal muscle mass. Combinations of IL-15 with other trophic factors are also encompassed by the invention. Typical animals that may have their muscle mass increased through the administration of IL-15 include farm animals, such as cows, pigs, sheep, chickens and salmon.

In addition to the above, the following examples are provided to illustrate particular embodiments and not to limit the scope of the invention.

EXAMPLE 1

Effect of IL-15 on Proliferation of C2 Myoblasts and Primary Bovine Myogenic Cultures This example describes the effect of IL-15 on the proliferation of C2 myoblast cells and primary bovine myogenic cultures. Simian IL-15 was prepared as described by Grabstein et al., Id. C2 myoblasts, a line of cells derived from adult murine skeletal muscle, were isolated according to methods described by Yaffe et al., *Nature*, 270:725 (1977). The C2 myoblasts were maintained in Eagle's Minimum Essential Medium (MEM; Sigma, St. Louis, Mo.) with 10% fetal calf serum (FCS; Hyclone, Logan, Utah). C2 myoblast cells were inoculated at 50,000 cells per 35 mm dish in 1.5 ml of 10% FCS in MEM. After 24 hours, the medium was changed to 1.5 ml of 0.5% FCS in MEM, and recombinant simian IL-15 was added in varying concentrations. Culture under these conditions continued for an additional 44 hours, followed by administration of 0.75 uCi of [$^3$H]-thymidine (6.7 Ci/mmol; New England Nuclear, Wilmington, Del.) for four hours. Incorporation of the [$^3$H]-thymidine radiolabel into the C2 cell DNA was determined using trichloroacetic acid (TCA) precipitation as described by Chen et al., *J. Cell Physiol.*, 160:563 (1994). That is, cultures were rinsed, DNA precipitated with 1 ml cold 5% TCA at 4° C. overnight, then rinsed with cold 5% TCA. DNA was solubilized with 1 ml of 0.5 M NaOH, transferred to scintillation vials containing 10 ml of Ecolume (ICN, Irvine, Calif.), neutralized with 100 μl of glacial acetic acid, and incorporation of label into DNA was quantified using a Packard 1900 CA Tri-Carb liquid scintillation analyzer.

Primary fetal bovine myogenic cultures were prepared from trypsin digests of cryopreserved 90-day fetal bovine thigh muscle as described by Quinn et al., *Devel. Biol.*, 140:8 (1990), which is incorporated herein by reference. Myogenic cells were inoculated at 100,000 cells per 35 mm dish in 1.5 ml of 10% FCS in MEM. After the cells were allowed to attach to the culture dishes for 48 hours, the medium was changed to 1.5 ml of 2% FCS in MEM, and varying concentrations of recombinant simian IL-15 were added. Assays for proliferation or for MHC expression were performed as described above using $[^3H]$-thymidine incorporation, at 24-hour intervals following the change to the low-serum medium and assays were continued for four days. Medium (1.5 ml of 2% FCS in MEM) and IL-15 were replenished after 48 hours.

Figure 1B:
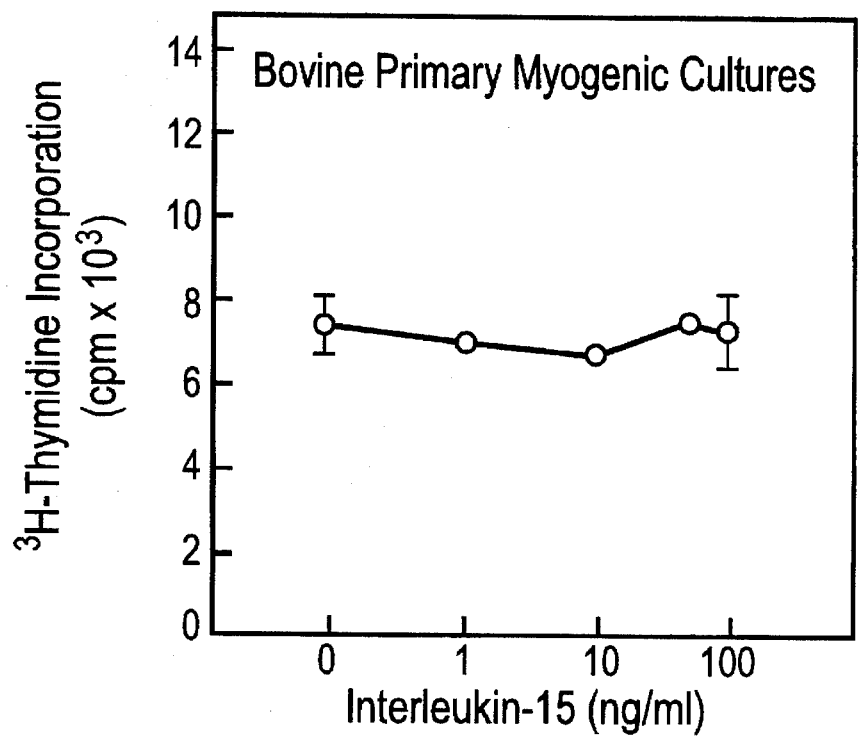

As shown in FIGS. 1A and 1B, $^3[H]$-thymidine incorporation assays indicated that at all concentrations of IL-15 tested, incorporation of label into DNA remained virtually unchanged. Thus, IL-15 had no effect on the proliferation of C2 myoblasts or primary bovine myogenic cultures at any concentration tested.

EXAMPLE 2

Effect of IL-15 on Differentiated Bovine Muscle Fibers With and Without IGF-I

This example describes the effect of IL-15 on differentiated bovine muscle fibers alone or in combination with IGF-I. Primary bovine myogenic cultures were inoculated as described in Example 1. The medium was changed to 2% FCS in MEM after 48 hours, and cells were allowed to differentiate and fuse. After 3 days following the switch to the low-serum medium, 5 μg/ml of the mitotic inhibitor aphidicolin (Sigma; Gosset et al., *J. Cell Biol.*, 106:2127 (1988)) was added with or without IL-15 or human recombinant IGF-I (UBI, Lake Placid, N.Y.). The medium and growth factors (IL-15 or IGF-I) were replenished 48 hours later, and cultures were harvested for Western blot analyses or fixed for immunocytochemical analyses of MHC expression at 72 hours following the administration of aphidicolin and IL-15 or IGF-I. Thus, differentiated myocytes/muscle fibers were treated with IL-15 or IGF-I for 72 hours.

Figure 2:
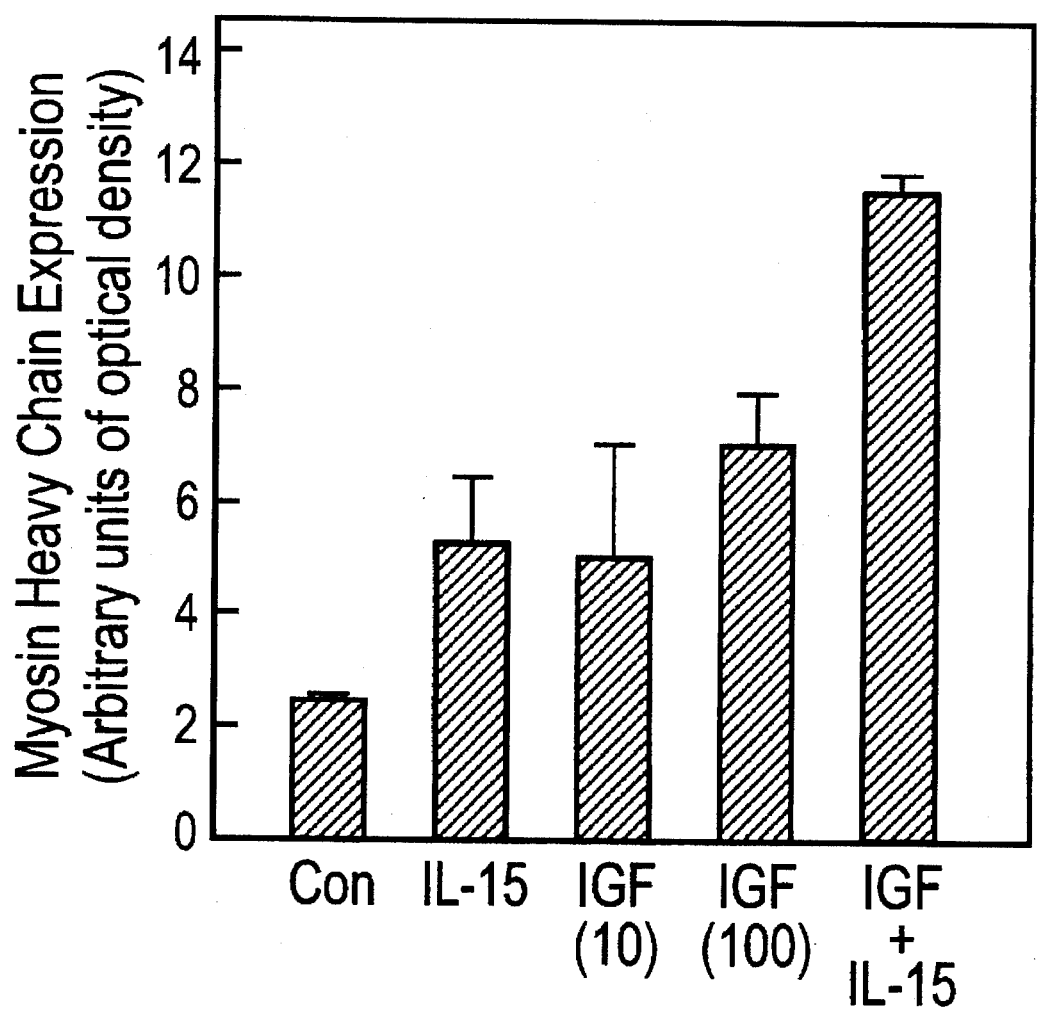
FIG. 2 illustrates the effects of IL-15 and IGF-I on muscle-specific myosin heavy chain (MHC) accumulation by differentiated primary bovine muscle cultures, assessed by densitometric quantitation of Western blots. Well-fused bovine myogenic cultures treated with the mitotic inhibitor, aphidicolin, were administered IL-15 or IGF-I for 72 hours as follows: Con: no treatment; IL-15: IL-15 administered at 10 ng/ml; IGF-I (10): IGF-I administered at 10 ng/ml; IGF-I (100): IGF-I administered at 100 ng/ml; and IGF-I+IL-15: IL-15 administered at 10 ng/ml and IGF-I administered at 100 ng/ml. The first four bars represent the means ± SEM for three independent experiments; the fifth bar represents the mean ± SEM of two independent experiments.

The aphidicolin inhibited $^3[H]$-thymidine incorporation completely. In addition, inverted phase microscopic evaluation of the cultures indicated that aphidicolin treatment resulted in death of cycling cells, leaving cultures predominantly composed of fused myotubes. As shown in FIG. 2, cultures treated with 10 ng/ml of IL-15 contained about twice as much MHC as the control. In addition, IL-15 was as effective as 10 and 100 ng/ml of IGF-I in stimulating MHC expression. The combination of 10 ng/ml of IL-15 and 100 ng/ml of IGF-I was additive and was more effective than either IL-15 or IGF-I alone, increasing MHC expression almost five-fold over that of the control. Since the action of IL-15 was additive to that of IGF-I utilized at saturating concentrations, these findings suggest that IL-15 does not act by inducing myocytes to increase autocrine expression of IGF-I and also demonstrate that IL-15 can act directly on differentiated muscle fibers.

EXAMPLE 3

Figure 3A:
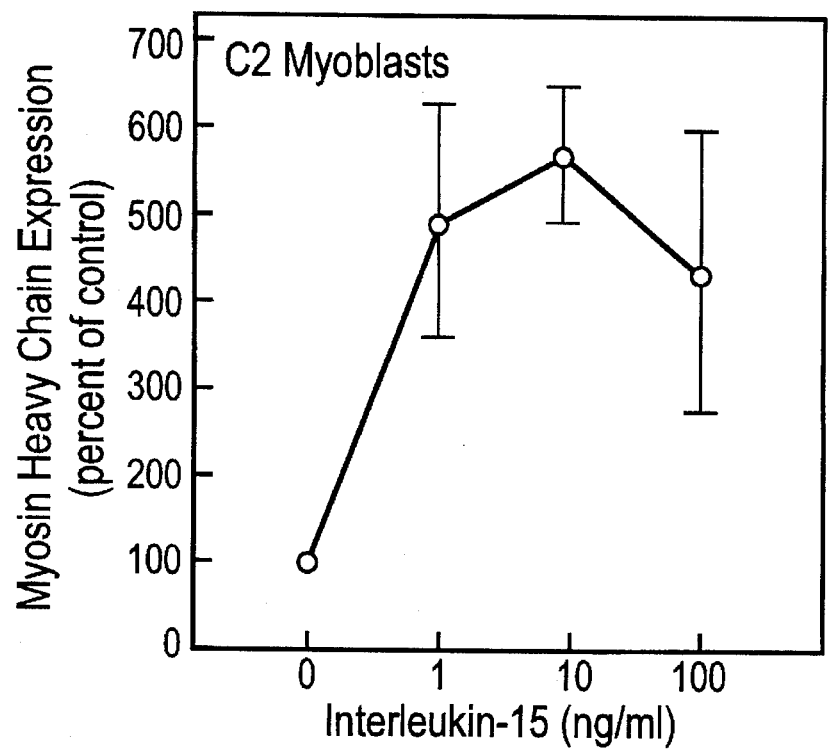
FIG. 3 shows they dose response effect of IL-15 MHC expression. Data shown in FIG. 3A and FIG. 3B are percent of control MHC expression in C2 myoblasts and primary bovine myogenic cultures, respectively, assessed by densitometric quantitation of Western blots, with each point representing the mean ± SEM of two independent experiments for each cell type. All determinations were made after exposure to IL-15 for four days.
Figure 3B:
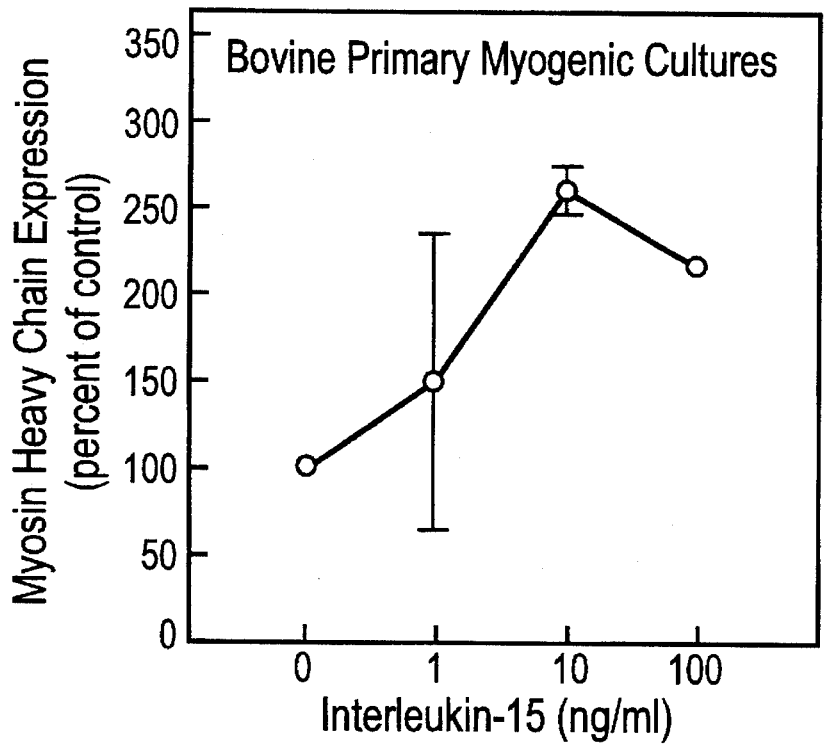
Figure 4A:
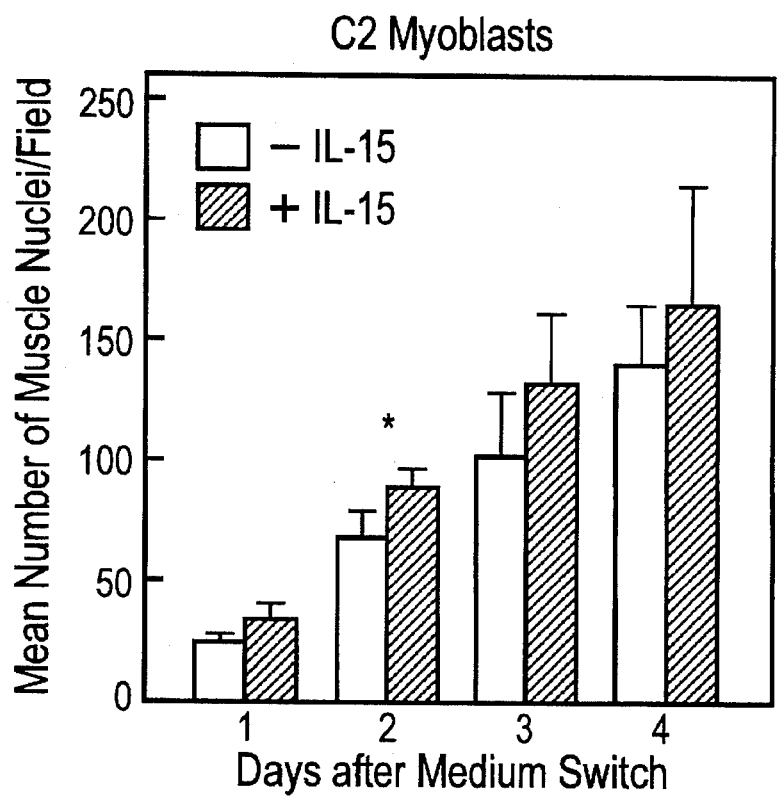
FIG. 4 illustrates the effects of IL-15 on the rate of myogenic differentiation. Differentiated myocyte nuclei were quantified at 24-hour intervals following the change to low-serum medium in C2 myoblast cultures (FIG. 4A) and primary bovine myogenic cultures (FIG. 4B) using anti-MHC immunocytochemical assays. Data represent means ± SEM (n=12). The differences between controls and cultures treated with 10 ng/ml of IL-15 at each time point were compared using Student's t-test. In both sets of cultures, the day 2 values ± IL-15 were statistically different at $p \leq 0.05$. All other pairs were not statistically different.
Figure 4B:
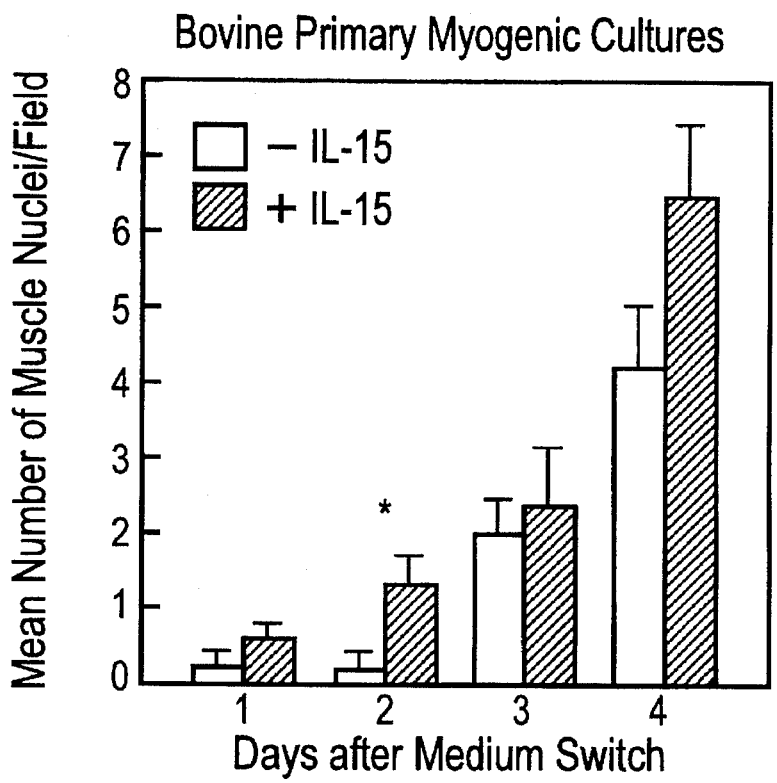

Effect of IL-15 on Differentiation and MHC Expression of C2 Myoblasts and Primary Bovine Myogenic Cultures C2 myoblasts and primary bovine myogenic cultures were innoculated as described in Example 2, except that aphidocolin was not used. MHC was quantified by Western blots as described above, and immunocytochemical assays were performed as described above. As shown in FIGS. 3 and 4, varying concentrations of recombinant simian IL-15 stimulated expression of MHC. MHC expression was increased approximately five-fold in mouse C2 myoblast cultures (FIG. 3), and approximately 2.5-fold in primary fetal bovine myogenic cultures (FIG. 4) when IL-15 was utilized at a concentration of about 10 ng/ml. To determine if this stimulation of MHC expression was due to an increase in the rate of myogenic differentiation, the time course of appearance of myocyte nuclei was determined using conventional anti-MHC immunocytochemistry. As shown in FIGS. 3 and 4, the numbers of terminally differentiated, myocyte nuclei detected at day 2 in both C2 myoblast and primary bovine myogenic cultures treated with 10 ng/ml of IL-15 were significantly different from their respective controls. It is possible that this effect may be due to a slight increase in immunocytochemical detectability of myosin expression in newly-differentiating myocytes. However, the differences observed cannot account for the approximately five-fold and 2.5-fold increases in MHC expression in C2 myoblasts and primary bovine myogenic cultures, respectively, observed using Western blots. While the data indicate that IL-15 may stimulate myogenic differentiation, the data indicate that IL-15 mainly acted to stimulate MHC expression or accumulation in differentiated myocytes.

Additionally, in data not shown, myotubes in IL-15-treated C2 myoblast cultures appeared larger than those in the control cultures. This observation indicates that IL-15 stimulates overall muscle fiber hypertrophy and not simply MHC accumulation. These results indicate that IL-15 has no effect on the rates of myoblast proliferation, but does act to stimulate muscle-specific MHC accumulation in differentiated myocytes.

What is claimed is:

1. A composition comprising a muscle-trophic amount of interleukin-15 (IL-15) and a muscle-trophic amount of a factor selected from the group consisting of a steroid, growth hormone and insulin-like growth factor (IGF-I), and a physiologically-acceptable carrier or diluent.

2. A composition according to claim 1, wherein the factor is growth hormone.

3. A composition according to claim 1, wherein the factor is IGF-I.

4. A method of stimulating muscle growth in a vertebrate comprising administering a muscle-trophic amount of IL-15.

5. A method of stimulating muscle growth according to claim 4, the composition further comprising a muscle-trophic amount of a factor selected from the group consisting of a steroid, growth hormone and insulin-like growth factor (IGF-I).

6. A method according to claim 4, wherein the vertebrate is a human.

7. A method according to claim 4, wherein the vertebrate is selected from the group consisting of chicken, ovine, bovine, porcine and fish.

8. A method of stimulating muscle growth in a vertebrate suffering from congestive heart failure comprising administering a muscle-trophic amount of IL-15.

9. A method of treating congestive heart failure according to claim 8, the composition further comprising a muscle-trophic amount of a factor selected from the group consisting of a steroid, growth hormone and insulin-like growth factor (IGF-I).

10. A method of stimulating muscle growth in a vertebrate suffering from disuse atrophy comprising administering a muscle-trophic amount of IL-15.

11. A method of treating a disuse atrophy according to claim 10, the composition further comprising a muscle-trophic amount of a factor selected from the group consisting of a steroid, growth hormone and insulin-like growth factor (IGF-I).

12. A method of stimulating muscle growth in a vertebrate suffering from muscle wasting comprising administering a muscle-trophic amount of IL-15.

13. A method of treating muscle wasting according to claim 12, the composition further comprising a muscle-trophic amount of a factor selected from the group consisting of a steroid, growth hormone and insulin-like growth factor (IGF-I).

14. A method of stimulating muscle growth in a vertebrate suffering from diabetes-associated glucose intolerance comprising administering a muscle-trophic amount of IL-15.

15. A method of treating diabetes-associated glucose-intolerance according to claim 14, the composition further comprising a muscle-trophic amount of a factor selected from the group consisting of a steroid, growth hormone and insulin-like growth factor (IGF-I).

16. A method of stimulating muscle growth in a vertebrate suffering from diabetes-associated dyslipidemia comprising administering a muscle-trophic amount of IL-15.

17. A method of treating diabetes-associated dyslipidemia according to claim 16, the composition further comprising a muscle-trophic amount of a factor selected from the group consisting of a steroid, growth hormone and insulin-like growth factor (IGF-I).

18. A method of stimulating muscle growth in a vertebrate suffering from rhabdomyosarcoma comprising administering a muscle-trophic mount of IL-15.

19. A method of treating rhabdomyosarcoma according to claim 18, the composition further comprising a muscle-trophic amount of a factor selected from the group consisting of a steroid, growth hormone and insulin-like growth factor (IGF-I).

20. A method of stimulating muscle growth in a vertebrate suffering from muscular dystrophy comprising administering a muscle-trophic amount of IL-15.

21. A method of treating rhabdomyosarcoma according to claim 20, the composition further comprising a muscle-trophic amount of a factor selected from the group consisting of a steroid, growth hormone and insulin-like growth factor (IGF-I).

* * * * *